(12) United States Patent
Weinberg

(10) Patent No.: US 8,460,183 B2
(45) Date of Patent: Jun. 11, 2013

(54) DE-LOOPING TOOL FOR AN ENDOSCOPE

(76) Inventor: Andrew Mark Weinberg, Tucson, AZ (US)

(\*) Notice: Subject to any disclaimer, the term of this patent is extended or adjusted under 35 U.S.C. 154(b) by 585 days.

(21) Appl. No.: 12/617,107

(22) Filed: Nov. 12, 2009

(65) Prior Publication Data

US 2010/0125169 A1     May 20, 2010

Related U.S. Application Data

(60) Provisional application No. 61/115,154, filed on Nov. 17, 2008.

(51) Int. Cl.
*A61B 1/00* (2006.01)

(52) U.S. Cl.
USPC ........................................ 600/144; 600/104

(58) Field of Classification Search
USPC .................. 600/104, 144, 121, 125, 139, 140
See application file for complete search history.

(56) References Cited

U.S. PATENT DOCUMENTS

| | | | | |
|---|---|---|---|---|
| 5,308,354 A | * | 5/1994 | Zacca et al. | 606/159 |
| 6,168,579 B1 | * | 1/2001 | Tsugita | 604/96.01 |
| 6,790,173 B2 | * | 9/2004 | Saadat et al. | 600/114 |

\* cited by examiner

*Primary Examiner* — Alireza Nia

(57) ABSTRACT

A method and apparatus for removing loops formed during endoscopic procedures including colonoscopy and small bowel enteroscopy. The device inserted through the biopsy channel of an endoscope reversibly engages the distal portion of the biopsy channel of the endoscope. When pressure is applied to the device handle external to the endoscope, the force is transmitted to the distal end of the endoscope advances and straightens out the loop. When the device is torqued, the distal end of the engaged endoscope torques which can remove a twist in the endoscope as well. Neither procedure requires removal of a portion of the scope or loss of position which occurs with conventional methods.

9 Claims, 6 Drawing Sheets

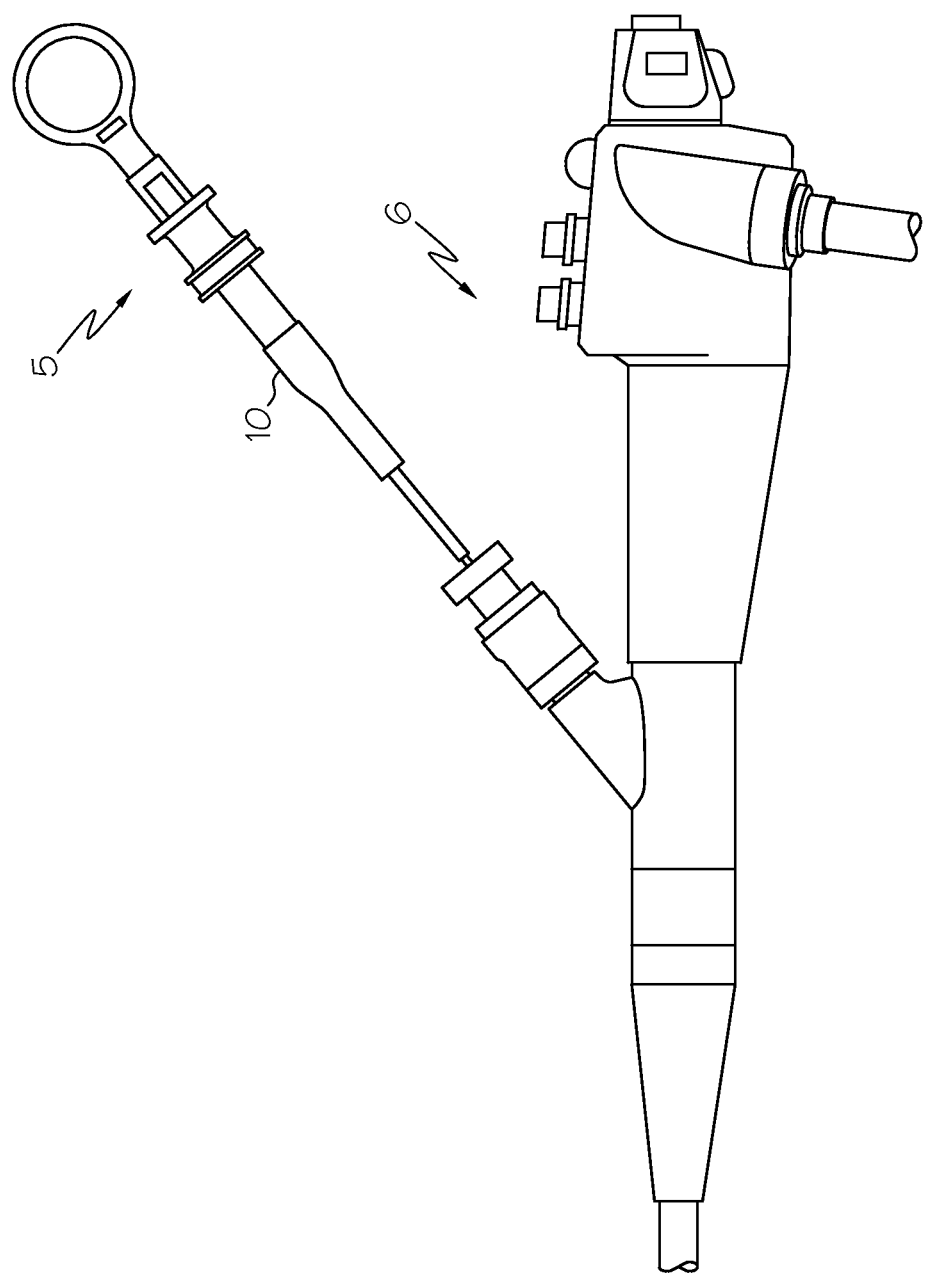

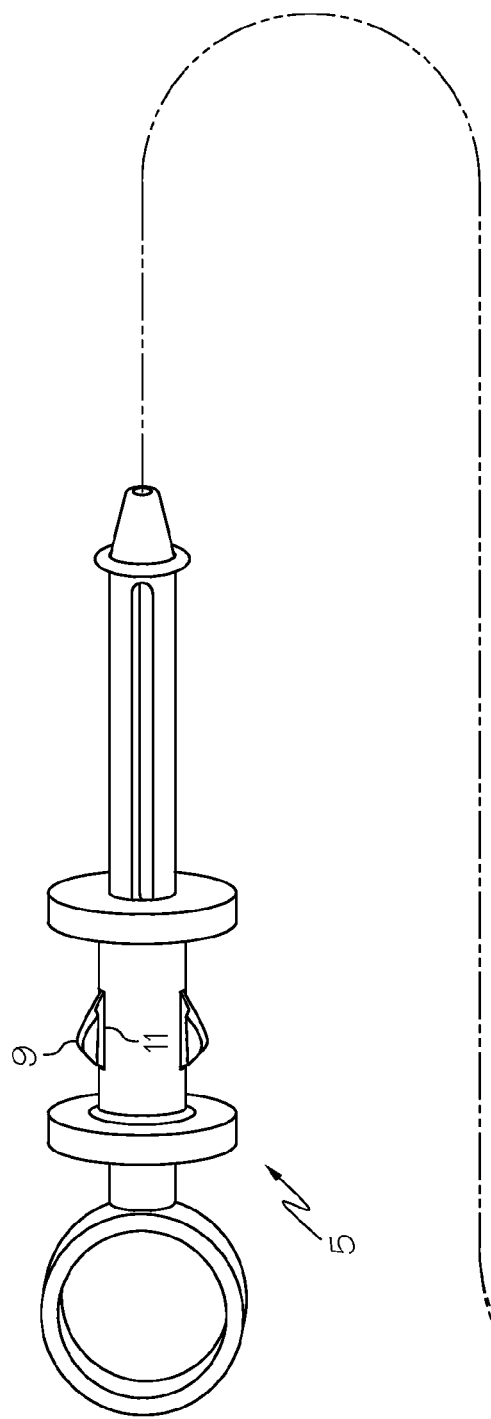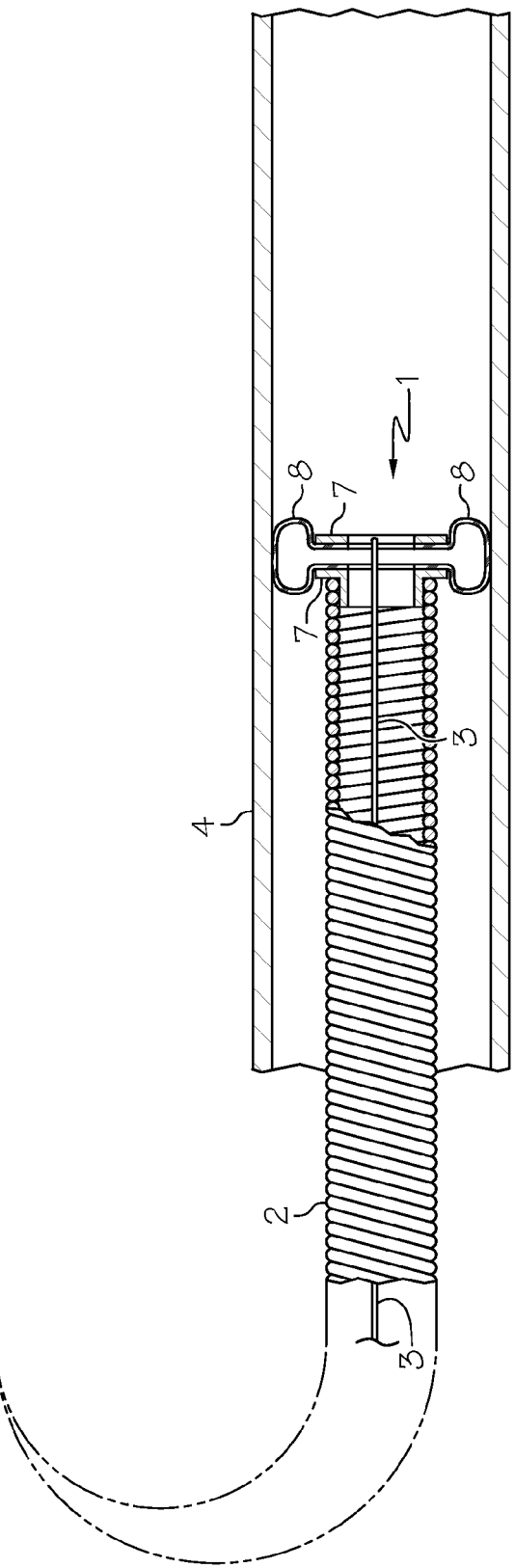
FIG. 4B

DE-LOOPING TOOL FOR AN ENDOSCOPE

CROSS REFERENCE TO RELATED APPLICATIONS

This application claims the cross benefit of U.S. Provisional Patent Application No. 61/115,154, which is incorporated by reference herein.

FIELD OF THE INVENTION

The field of the invention is a tool for endoscopic procedures. These include colonoscopy, upper endoscopy, endoscopic ultrasound etc.

BACKGROUND

Endoscopy procedures are used by physicians worldwide to assist in surgeries and various medical procedures including colonoscopy, upper endoscopy (esophagogastroduodenoscopy), bronchoscopy, thoracoscopy, laparoscopy, heart catherization, nasopharyngoscopy etc. As the endoscope is advanced from the proximal end by the operator, the distal end (tip) usually advances. However, at times especially around tight turns a loop forms which prevents the distal end from advancing with advancement of the proximal end. Any of the following are endoscopes: colonoscope, gastroscope, enteroscope, bronchoscope, endoscopic ultrasound endoscope, laparoscope, thoracoscope). During these procedures sometimes the scope bends unpredictably from friction and forms a loop. This loop may prevent advancement of the scope by the operator and result in bowel distention from the loop which can cause patient discomfort.

SUMMARY OF THE INVENTION

There is a need to minimize formation of these loops. Current technology requires the operator (physician) to remove the loop by twisting and or withdrawing the scope until the loop disappears. In addition, the patient position may be changed such as rolling the patient onto their back or belly or by applying abdominal pressure as in the case of colonoscopy. These maneuvers change the friction applied to the scope by the body and effect of gravity on the scope and these maneuvers take time to perform. Sometimes the maneuvers are sufficient to finish the procedure. Other times additional sedation must be administered due to patient discomfort from the loop(s) and the patient will have a longer recovery time from the extra sedation. Current techniques can be time consuming and not always successful. In colonoscopy, additional pressure is applied to the belly and the patient is rolled from side to side to attempt to remove these loops. Sometimes the procedure is aborted due to patient discomfort from looping and or inability of the physician to be able to complete the procedure due to the loops. There is a need for a de-looping tool to allow removal of the loops without re-orienting the patient, removing a portion of the scope, applying abdominal pressure, giving additional sedation due to increased patient discomfort from the formation of loops during the procedure, or even starting over.

DETAILED DESCRIPTION

Figure 1A:
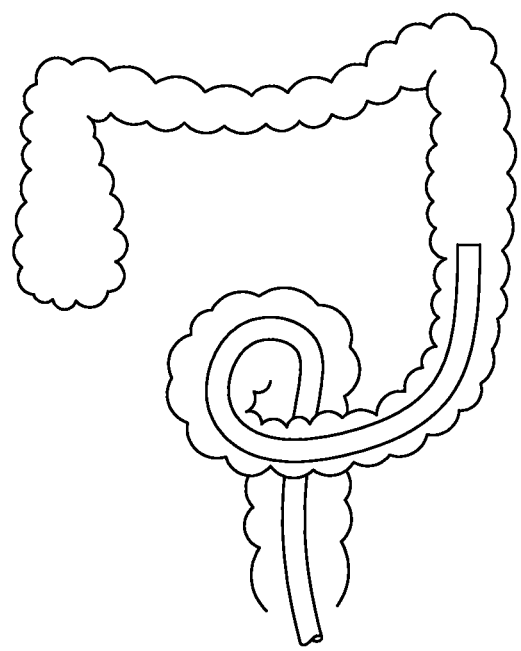
FIG. 1A Alpha Loop
FIG. 1B N shaped loop
FIG. 2 Endoscope with tool inserted in biopsy channel
FIG. 3A Handle in unlocked (unactuated) position
FIG. 3B Handle in locked (actuated) position
FIG. 4A Tool in biopsy channel unactuated and able to be repositioned or removed.

The figures below show an alpha loop (FIG. 1A) and an N-loop (FIG. 1B) which can occur during endoscopy. In either case, as the proximal end of the scope 6 is advanced, the distal (tip) end does not advance and the loop becomes larger. Sometimes the only way to get the tip of the scope to advance is to remove the loop entirely which may require removing all of the endoscope and starting over. Other times the loop expands but the operator is able to complete the procedure anyway, although additional sedation may be required due to ensuing patient discomfort. The de-looping tool 1 attaches to the distal end of the scope 6 internally through the scope's biopsy channel 4. As force is applied to the tool by inserting a wire 3 into the biopsy channel 4 the tip of the scope is advanced since the attachment point is at the tip. Thus the tool 1 works by applying pressure near the tip of the tool as opposed to the proximal end of the endoscope 6 where the operator usually applies pressure. There are various ways of reversibly attaching the de-looping tool 1 to the endoscope 6. In all cases an internal tool 1 is used to affix to the endoscope 6. In case the tool slips, the tool remains inside of the endoscope and is not long enough to exit the endoscope biopsy channel and thus tool slippage will not harm the patient. This is an important safety consideration. One mechanism for attaching the tool to end of the scope is an umbrella apparatus which deploys when actuated in the channel. A second design has an expandable jack similar to a car jack used for changing a tire. A third design which is likely the simplest and most cost effective is a compressible foam or substantially compressible alternate material such as synthetic or natural rubber which expands radially to engage the biopsy channel when compressed in a linear direction. The material must substantially return to its original shape when the compression force is released to allow the tool to be removed.

Preferred Embodiment

In the preferred embodiment, a wire based tool 1 made of a metal, alloy metal, plastic, and/or a polymer may be either tightly coiled such as in many colonoscopy biopsy tools or a linear flexible yet strong metal wire is used. An outside flexible sleeve 2 of tightly coiled wire surrounds an inner linear wire 3. The wire 3 may also be coiled and tightly wound for added flexibility or may be linear in shape. The sleeve 2 nearly fills the entire biopsy channel 4 for maximum strength. A handle 5 shaped to allow easy advancement of the wire 3 and sleeve 2 against resistance is used. The handle 5 may have various shapes such as loops, holes for fingers, a flat surface or a curved surface. Most likely the handle 5 would be made out of a strong plastic which is cost effective and durable. The wire 3 and sleeve 2 portion outside of the endoscope 6 attached to the handle 5 is reinforced to minimize kinking or bending of the wire when force is applied to the handle 5. Near the distal end of the endoscope 6, but before the highly articulate distal end of the endoscope 6, the attachment apparatus will reversibly engage the biopsy channel 4. Typically the de-looping tool 1 reversibly and non destructively engages the biopsy channel 4 about 10-15 cm from the distal end (scope tip) of the endoscope body. The sleeve 2 and wire 3 both have an annular lip 7 which can be a plastic, alloy, or metal washer affixed. The sleeve lip 7 is proximal and the wire lip 7 is distal. In between the lips 7 threaded over the wire 3 is a closed cell foam or rubber cylindrically shaped compressible piece 8 attached to lips 7 at its proximal and distal portions. Other shapes of the compressible piece may include any shaped polygon. Typically, this portion of compressible foam 8 may be 2-3 cm long but my be of any length desired.

Figure 3B:
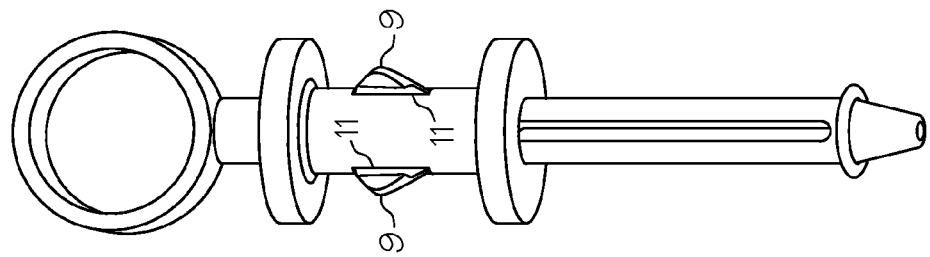
Figure 3A:
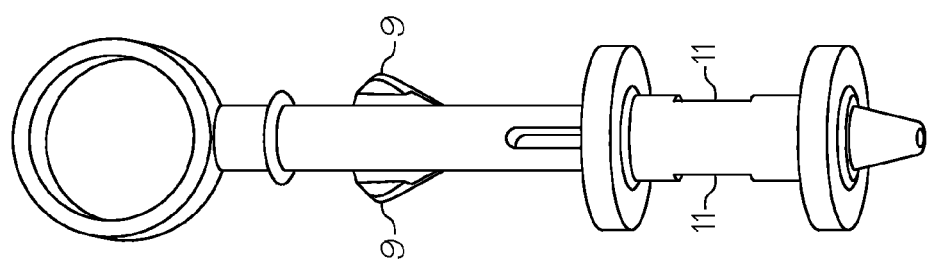
Figure 4A:
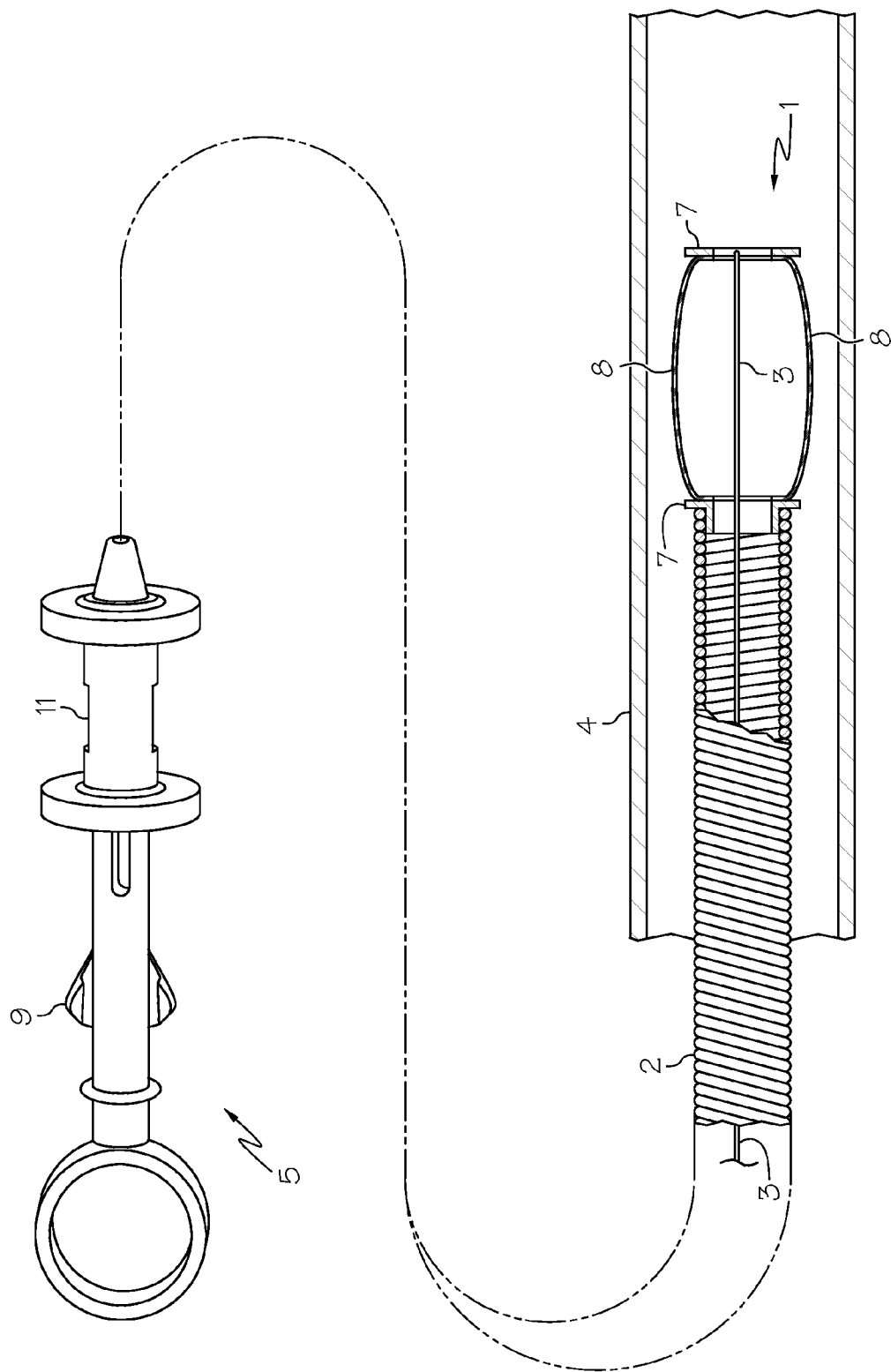
FIG. 4B Tool in biopsy channel actuated and locked in position
FIG. 5 Overall picture of tool
Figure 5:
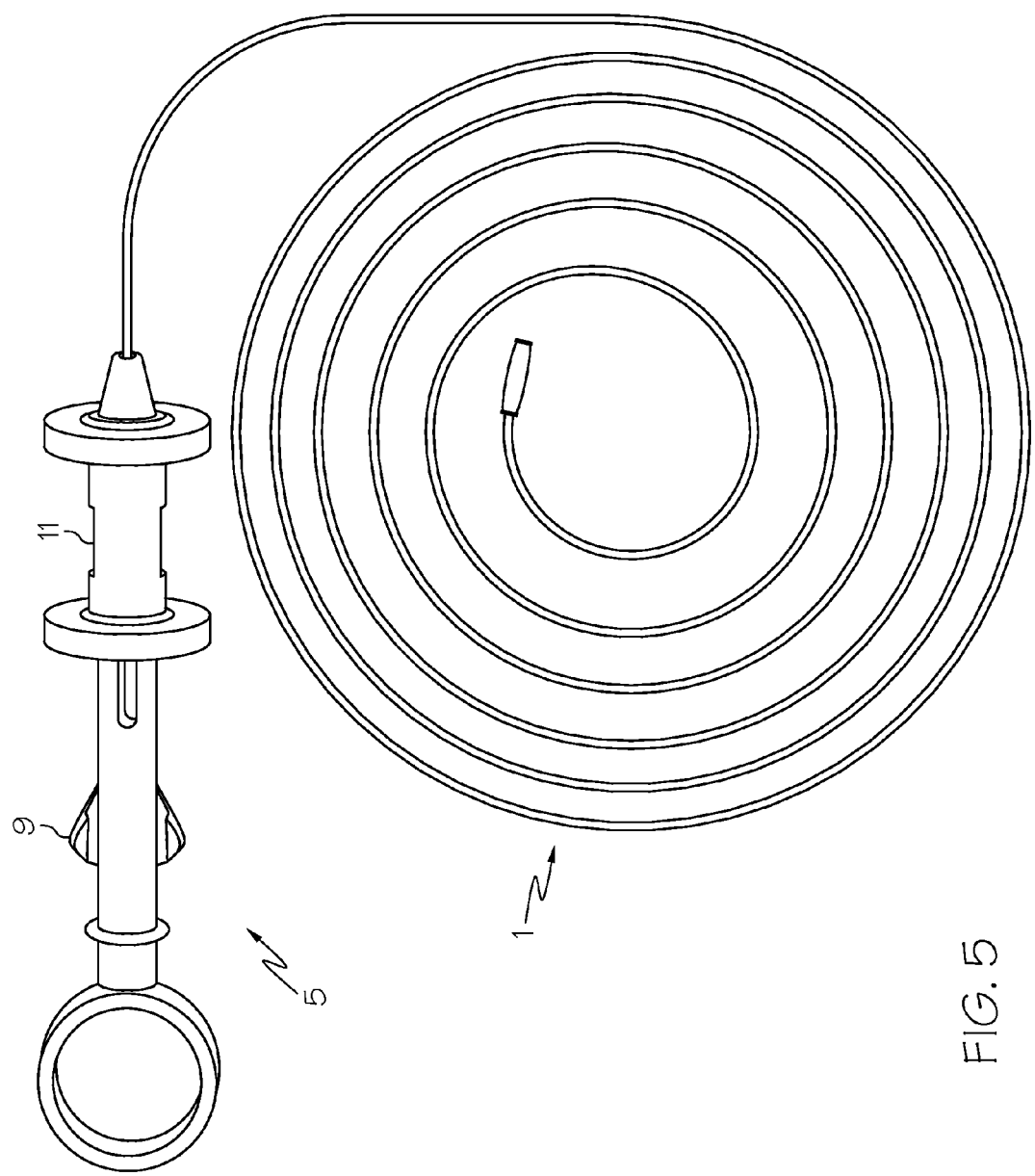

In operation, the tool 1 (FIG. 5) is inserted into an endoscope 6 (FIG. 2) such as a colonoscope that has a loop. The tool handle 5 is initially undeployed (unactuated FIG. 3A) such that the lips 7 of the sleeve 2 and wire 3 are far apart stretching the compressible piece (foam) 8 to allow easy insertion of the tool 1. The tool 1 is inserted until the handle 5 is perhaps a half inch from resting on the biopsy insertion channel opening. At that time the handle 5 is placed in the actuated position (FIG. 3B) and locked into place by flexible tabs 9 engaging slots 11. In the actuated position, the wire 3 is drawn towards the sleeve 2 and the two lips 7 compress the compressible piece 8. The excess material from the compressible piece 8 expands radially outward and engages biopsy channel 4. The lock 9 on handle 5 allows the operator to avoid manually applying force to continue engaging tool 1 against biopsy channel 4. The tool handle 5 is held by a physician or technician and pressure to advance handle 5 is applied in the locked (actuated) position (FIG. 4B). However, handle 5 does not advance since compressible foam 8 is attached to the biopsy channel 4. The resulting force is transmitted to the tip of scope 6 at the point of the engagement with biopsy channel 4 and the loop is removed by the tip of scope 6 moving forward. To remove the tool 1, the tool 1 is unlocked (unactuated) by pressing in tabs 9 into slots 11, the tension pulling the distal lip 7 against the proximal lip 7 is removed and compressible material 8 no longer expands in a radial direction (FIG. 4A). The biopsy channel 4 is no longer engaged and tool 1 is simply removed.

Figure 1B:
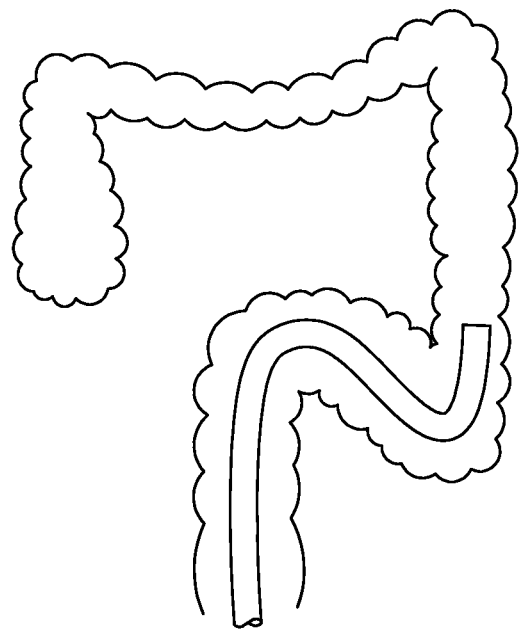

The portion of wire 3 inserted through the deformable material (foam) 8 may be of reduced diameter to allow additional deformable material to be applied. The de-looping tool 1 may be engaged at any distance into scope 6 desired by the operator by engaging the sleeve at that particular location. The insertion wire 3 may have paint marks or etchings at specific distances to allow the operator to easily estimate engagement depth. An external sleeve 10 outside of the endoscope 6 may be used to help minimize kinking of the de-looping tool 1. This is important when advancement pressure is applied to handle 5 once tool 1 is actuated (engaged) with biopsy channel 4. The tool 1 is designed to have a non destructive and reversible engagement to minimize wear or damage risk to the endoscope 6. The de-looping tool 1 can be used on any conventional endoscope 6 listed above as well as scopes being designed for NOTES (natural orifice transluminal endoscopic surgery) procedures. Torque may be applied to the de-looping tool 1 to remove an alpha loop which is a twisted loop (FIG. 1A). The method can also be used to minimize formation of an N-loop (FIG. 1B) by applying light pressure to the distally engaged de-looping tool 1 while advancing the proximal end of scope 6. This maneuver may be particularly useful when navigating around tight turns etc. which may normally tend to form loops.

What is claimed is:

1. A De-looping tool, comprising:
   a handle portion;
   a sleeve portion attached to said handle at a proximal end with a sleeve annular lip at a distal end of said sleeve portion;
   a coiled wire portion with a proximal end and a distal end;
   a wire annular lip at said distal end of said coiled wire portion and said proximal end of the coiled wire portion being attached to said handle;
   wherein said coiled wire portion is inserted through said sleeve portion, wherein a portion of said coiled wire protrudes from said sleeve portion at said distal end of said sleeve portion, wherein said wire annular lip and said sleeve annular lip encompasses the majority of an endoscope biopsy channel and wherein said sleeve annular lip is proximal to said wire annular lip relative to said handle portion; and
   wherein a reversibly expandable cylindrically or other polygonal shaped foam attached to said sleeve annular lip at a proximal end of said foam and attached to said wire annular lip at a distal end of said foam, wherein said expandable foam surrounds a portion of said protruding coiled wire portion, wherein said sleeve annular lip is capable of being advanced toward said wire annular lip to compress said foam; and
   wherein said sleeve and handle portions, when inserted into said endoscope biopsy channel, is too short in length to protrude out a distal end of said endoscope biopsy channel.

2. The De-looping tool of claim 1, wherein said De-looping tool is actuated in an endoscope biopsy channel by retracting said handle which pulls said wire further inside of said sleeve compressing said foam between said sleeve annular lip and said wire annular lip reversibly compressing said foam against said biopsy channel of an endoscope to fix a position of said tool with respect to said endoscope.

3. The De-looping tool of claim 2, wherein said foam is capable of reversibly expanding radially relative to said wire and engage a biopsy channel of an endoscope when said sleeve annular lip and said wire annular lip compress said foam upon actuating said De-looping tool in an endoscope.

4. The De-looping tool of claim 3, wherein said foam is natural or synthetic rubber, plastic, or composite material.

5. The De-looping tool of claim 2, wherein said De-looping tool can be reversibly locked in said actuated position by a lock mechanism on said handle.

6. The De-looping tool of claim 2, wherein said De-looping tool is unactuated by releasing said lock mechanism on said handle.

7. The De-looping tool of claim 1 wherein said handle is made of plastic and is attached to said sleeve and said wire.

8. A method of reversibly and nondestructively affixing a De-looping tool in a biopsy channel of an endoscope capable of moving a tip of said endoscope, comprising:
   selecting an endoscope with a biopsy channel; AND
   inserting a De-looping tool into said biopsy channel, wherein said De-looping tool comprises:
   a handle portion;
      a sleeve portion attached to said handle at a proximal end with a sleeve annular lip at a distal end of said sleeve portion;
      a coiled wire portion with a proximal end and a distal end;
      a wire annular lip at said distal end of said coiled wire portion and said proximal end of the coiled wire portion being attached to said handle;
      wherein said coiled wire portion is inserted through said sleeve portion, wherein a portion of said coiled wire protrudes from said sleeve portion at said distal end of said sleeve portion, wherein said wire annular lip and said sleeve annular lip encompasses the majority of an endoscope biopsy channel and wherein said sleeve annular lip is proximal to said wire annular lip relative to said handle portion; and wherein a reversibly expandable cylindrically or other polygonal shaped foam attached to said sleeve annular lip at a proximal end of said foam and attached to said wire annular lip at a distal end of said foam, wherein said expandable foam surrounds a portion of said protruding coiled wire portion, wherein said sleeve annular lip is capable of being advanced toward said wire annular lip to compress said foam; and wherein said sleeve and handle portions when inserted into said endoscope biopsy channel, is too short in length to protrude out a distal end of said endoscope biopsy channel;

actuating said De-looping tool such that a tip of said De-looping tool engages walls of said biopsy channel thereby affixing a position of said De-looping tool within said endoscope with a said foam, and wherein said De-looping tool is capable of transmitting an axial force on said endoscope when force is applied to said handle on said De-looping tool capable of moving said endoscope.

9. The method of claim 8, further comprising:

an unactuated position wherein said De-looping tool may move freely within said biopsy channel, and a reversible lock on said handle of said De-looping tool that maintains actuated or unactuated positions of said De-looping tool.

* * * * *